(12) United States Patent
Craen et al.

(10) Patent No.: US 8,100,592 B2
(45) Date of Patent: Jan. 24, 2012

(54) HOUSING FOR VARIABLE LENS

(75) Inventors: Pierre Craen, Embourg (BE); Nicolas Tallaron, Lyons (FR); David Perennez, Lyons (FR)

(73) Assignee: Varioptic, S.A., Lyons (FR)

( * ) Notice: Subject to any disclaimer, the term of this patent is extended or adjusted under 35 U.S.C. 154(b) by 0 days.

(21) Appl. No.: 12/600,112

(22) PCT Filed: May 6, 2008

(86) PCT No.: PCT/EP2008/055579
§ 371 (c)(1),
(2), (4) Date: Jun. 16, 2010

(87) PCT Pub. No.: WO2008/138811
PCT Pub. Date: Nov. 20, 2008

(65) Prior Publication Data
US 2010/0247086 A1    Sep. 30, 2010

(30) Foreign Application Priority Data
May 14, 2007   (EP) ................................. 07301038

(51) Int. Cl.
*G03B 17/00* (2006.01)
(52) U.S. Cl. .................. 396/439; 396/542; 359/666
(58) Field of Classification Search .............. 396/529, 396/439, 542; 359/666
See application file for complete search history.

(56) References Cited

U.S. PATENT DOCUMENTS
4,466,706 A  8/1984  Lamothe, II
6,392,827 B1  5/2002  Ueyama et al.
(Continued)

FOREIGN PATENT DOCUMENTS
EP   1 662 276 A1   5/2006
(Continued)

OTHER PUBLICATIONS
International Search Report from PCT/EP2008/055579 dated Nov. 17, 2008 (5 pages).

*Primary Examiner* — Christ Mahoney
*Assistant Examiner* — Fang-Chi Chang
(74) *Attorney, Agent, or Firm* — Osha• Liang LLP

(57) ABSTRACT

The invention concerns A housing for a variable focus liquid lens (204) containing first and second immiscible liquids defining a liquid-liquid interface moveable by electrowetting by application of a voltage between first and second electrodes (206, 208) of the liquid lens, the housing comprising: a first portion (202) comprising a contact surface for contact with a circuit board (203); a second portion (211) for receiving the liquid lens, the second portion arranged to be moveable with respect to said first portion in a first direction parallel to an optical axis (Δ) of the liquid lens when said liquid lens is positioned in said housing; and first and second contacts (213, 216) for electrically coupling the circuit board to the first and second electrodes respectively of the liquid lens when said liquid lens is positioned in said housing, wherein each of the first and second contacts comprises a first conductive surface (215a, 218a) arranged to make contact with a second conductive surface (215b, 218b), said first and second conductive surfaces slidable with respect to each other in said first direction, so that the circuit board can be coupled to the first and second electrodes.

18 Claims, 3 Drawing Sheets

U.S. PATENT DOCUMENTS

| | | |
|---|---|---|
| RE39,874 E | 10/2007 | Berge et al. |
| 7,443,596 B1 | 10/2008 | Berge |
| 7,573,646 B2 | 8/2009 | Craen et al. |
| 2007/0072065 A1 | 3/2007 | Saugier et al. |
| 2008/0013187 A1* | 1/2008 | Craen et al. .................. 359/665 |
| 2008/0037973 A1 | 2/2008 | Jung |
| 2008/0165427 A1* | 7/2008 | Tseng et al. .................. 359/666 |
| 2008/0267603 A1* | 10/2008 | Jung et al. .................. 396/111 |

FOREIGN PATENT DOCUMENTS

| | | |
|---|---|---|
| EP | 1798578 A1 | 6/2007 |
| EP | 1801622 A1 | 6/2007 |
| WO | 2005/101901 A1 | 10/2005 |

* cited by examiner

HOUSING FOR VARIABLE LENS

FIELD OF THE INVENTION

The present invention relates to a housing for an electrowetting device, in particular to a housing for a variable focus liquid lens in which the focus is variable by electrowetting. The present invention also relates to a lens system and camera module comprising such a housing and to a method of manufacturing and calibrating the camera module.

BACKGROUND OF THE INVENTION

Variable focus liquid lenses are known in the art. Such lenses generally comprise a refractive interface between first and second immiscible liquids that is moveable by electrowetting. FIG. 1 reproduces FIG. 4 of European Patent Application EP1662276, and illustrates a known variable focal length lens 10. Lens 10 comprises two transparent windows 24, 38 facing each other and parallel to one another, and delimiting, at least in part, an internal volume 15 containing two immiscible liquids 16, 18, with different optical indices, defining an optical interface A, B in the form of a meniscus where they meet. The liquids 16, 18 have substantially equal densities, and one is preferably an insulating liquid, for example comprising oil or an oily substance, and the other is preferably a conducting liquid comprising for example an aqueous solution. The windows are for example transparent plates, made of an optical transparent material, e.g. glass.

Lens 10 further comprises a cap 30 connected to transparent window 38 and comprising a first cylindrical side wall 34. Lens 10 also comprises a body 12 having a symmetry of revolution about the optical axis (.DELTA.) of the lens. Body 12 is connected to transparent window 24 and comprises a second cylindrical side wall 20 of a diameter smaller than the diameter of the first cylindrical wall. Cap 30 forms a first electrode and body 12 comprises a second electrode. A gasket 50 is provided to ensure the tightness of the lens structure, positioned such that it is compressed between the first and second cylindrical side walls. In particular, gasket 50 is substantially L-shaped in cross-section, comprising a portion 54 compressed between the first and second cylindrical side walls and a portion 52 compressed between the cap and a top surface 42 of body 12, the top surface 42 comprising an opening defining a conical or cylindrical surface 48 where the interface between the two liquids is able to move.

The lens further comprises deforming portions 36 arranged to deform in response to a change in pressure of the liquids. The deforming portions for example comprise corrugated regions 36 formed in the upper wall 31 of the cap, the deforming portions having symmetry of revolution about the optical axis (Δ) of the lens. For example, the deforming portions comprise at least one circular ripple centred on the optical axis (Δ) of the lens. In this example the cap is for example made of a stamped metal, pressed into shape, e.g. stamped stainless steel. The thickness of the upper wall of the cap will depend on the expected variations of volume to compensate for the effects of expansion of the liquids. For example, a typical thickness of about 0.1 to 0.25 mm has shown good results for lenses whose outer diameters is below 20 mm.

Side wall 34 of the cap comprises a rim 56 crimped onto the body 12, which deforms the gasket 50 between the cap and a corner of body 12, and seals the cap 30 and the body 12. Other methods for sealing the cap onto the body are possible, for example it would be possible to glue the cap 30 onto the body 12.

Due to the electrowetting effect, it is possible, by applying a voltage between the cap 30 and body 16, to change the curvature of the refractive interface between the first liquid 16 and the second liquid 18, for example, from an initial concave shape as shown by dashed line A, to a convex shape as shown by solid line B. Thus rays of light passing through the cell perpendicular to the windows 24, 38 in the region of the refractive interface A, B will be focused more or less depending on the voltage applied.

When variable liquid lens 10 is used in a lens unit, it is generally combined with a number of separate fixed lenses so that the lens unit has the desired total optical power. Such fixed lenses increase the size of the lens unit along the optical axis Δ, which is a disadvantage in some applications where space is limited, such as in compact digital cameras or mobile telephones. The number of fixed lenses that are needed can be reduced if the optical power of variable lens 10 is increased by replacing windows 24 and 38, which are planar windows in the example of FIG. 1, with lenses having a fixed optical power. Such windows would be centred on an optical axis (Δ) of the variable focus lens 10.

However, a problem occurs when mounting such a lens unit to an image sensor. During calibration of the lens unit it is necessary to adjust the positioning of all of the fixed lenses in the lens unit with respect to the image sensor so that images formed on the image sensor are correctly focused. Due to the fixed lenses in the liquid lens, the positioning of the liquid lens must also be adjusted at the same time as the other fixed lenses. However, an electrical connection is required between the electrodes of the liquid lens and driving circuitry that generates the appropriate drive voltages to control the lens. The adjustment of the positioning of the lens unit and in particular of the liquid lens means that it is difficult to make the required electrical connections.

SUMMARY OF THE INVENTION

According to an aspect of the present invention, there is provided a housing for a variable focus liquid lens containing first and second immiscible liquids defining a liquid-liquid interface moveable by electrowetting by application of a voltage between first and second electrodes of the liquid lens, the housing comprising: a first portion comprising a contact surface for contact with a circuit board; a second portion for receiving the liquid lens, the second portion arranged to be moveable with respect to said first portion in a first direction parallel to an optical axis of the liquid lens when said liquid lens is positioned in said housing; and first and second contacts for electrically coupling the circuit board to the first and second electrodes respectively of the liquid lens when said liquid lens is positioned in said housing, wherein each of the first and second contacts comprises a first conductive surface arranged to make contact with a second conductive surface, said first and second conductive surfaces slidable with respect to each other in said first direction, so that the circuit board can be coupled to the first and second electrodes.

According to one embodiment of the present invention, the first conductive surfaces of the first and second contacts are formed of conductive layers lining first and second holes passing through said first portion, and said second conductive surfaces of the first and second contacts comprise first and second metal contacts positioned within said holes.

According to a further embodiment of the present invention the second portion comprises a plurality of arms spaced radially around an end of said second portion for holding said liquid lens in position, wherein said first and second metal contacts extend between adjacent ones of said arms to make contact with said first and second electrodes respectively of the liquid lens when said liquid lens is positioned in said housing.

According to yet a further embodiment of the present invention, the housing comprises a further pair of holes lined with a conducting layer and for receiving the metal contacts for coupling the electrodes of the liquid lens to the circuit board, wherein the further pair of holes are positioned such that when said first and second holes are aligned with one or more of said arms, said further pair of holes are aligned with spaces between said arms.

According to a further aspect of the present invention, there is provided a method of calibrating the focusing of a camera module comprising: adjusting the distance between the lens system and the image sensor and at the same time applying a given voltage to at least one of the first and second contacts to set the liquid-liquid interface of the liquid lens in a nominal position, the adjusting step comprising moving said second portion with respect to said first portion.

According to a further aspect of the present invention, there is provided a method of manufacturing a camera module comprising: focusing the lens system by moving the second portion to a final position with respect to the first portion; determining that in the final position the first and second holes are not aligned with said arms; and placing the metal contacts in said first and second holes to a position in which they contact said first and second electrodes.

BRIEF DESCRIPTION OF THE DRAWINGS

The foregoing and other purposes, features, aspects and advantages of the invention will become apparent from the following detailed description of embodiments, given by way of illustration and not limitation with reference to the accompanying drawings, in which.

DETAILED DESCRIPTION OF THE INVENTION

Throughout the description, relative terms such as "horizontal", "vertical", "underside", "top surface", "top end" and "bottom end", that depend on the particular orientation of the lens housing apply when the lens housing is orientated as shown in the figures, in other words with the housing of the lens arranged substantially vertically, with the end for connecting to a support or similar substrate facing downwards, and the opposite end that receives a light image facing upwards. Terms such as "inner" and "outer" are generally used to mean radially inwards towards the centre of the housing, or outwards away from the centre of the housing, respectively.

Figure 1:
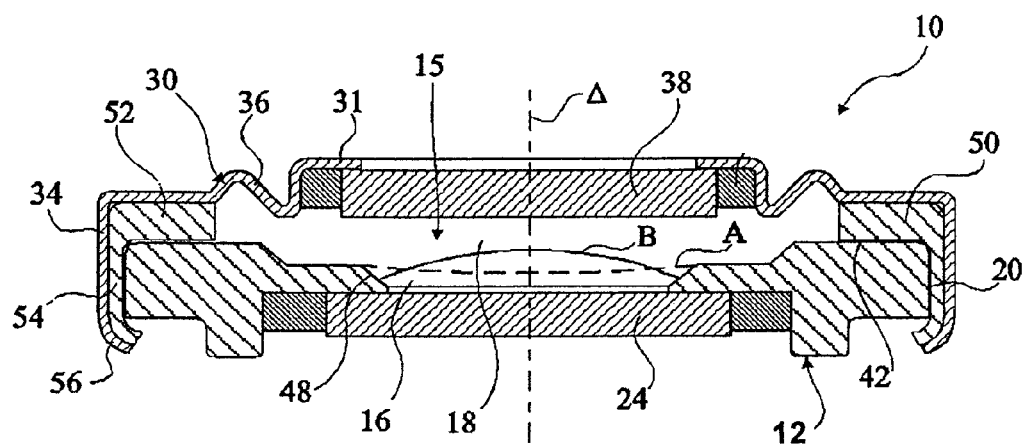
FIG. 1 (described above) is a cross-section view of a known liquid lens.
Figure 2:
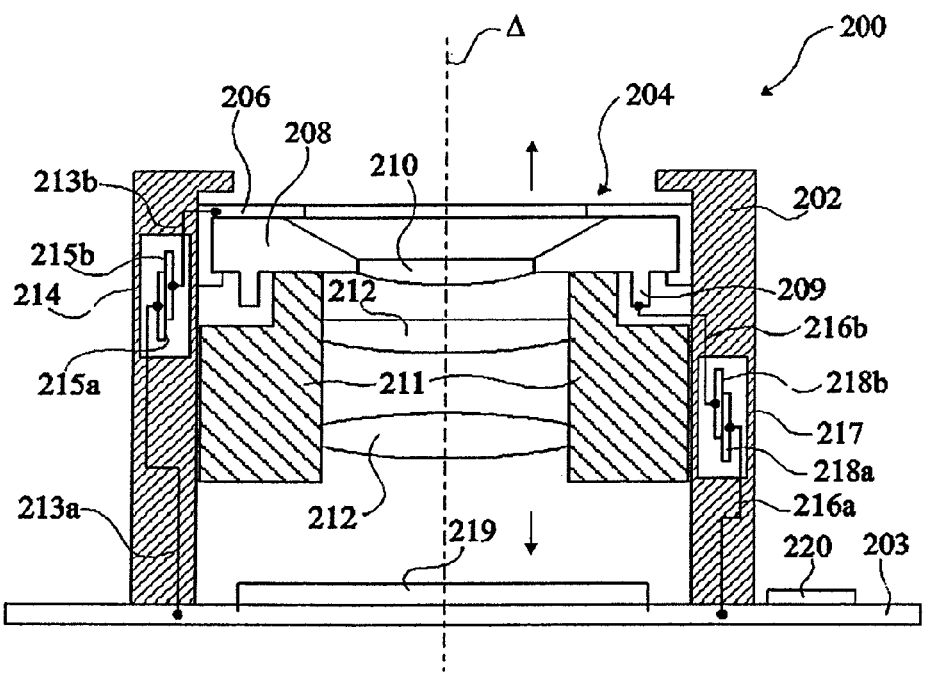
FIG. 2 is a schematic cross-section view of a camera module illustrating principles behind embodiments of the present invention.

With reference to FIG. 2, a camera module 200 is shown in cross-section, which is used to illustrate the principles of the embodiments described herein. Camera module 200 comprises an outer lens housing 202, which is for example a cylindrical component arranged to be mounted on a flat support 203, for example a PCB (printed circuit board). The outer lens housing 202 houses a number of lenses. In particular, a variable focus liquid lens 204 is positioned within the outer lens housing 202. Variable lens 204 is for example a liquid lens as described above in relation to FIG. 1 or as described in the corresponding European Patent Application EP 1662276, or for example as more generally described in European Patent No. EP1166157 or co-pending European applications 05112671 and 05112056.

In the present example the liquid lens is positioned in the outer lens housing 202 at the opposite end to the support 203, however in alternative embodiments other positions are possible. The liquid lens 204 comprises two electrodes, labelled 206 and 208. Electrode 206 is preferably part of a cap portion of the liquid lens 204 and electrode 208 is preferably an annular electrode having an annular foot 209 that extends from the underside of the lens.

By providing a contact surface on an annular foot 209, contact with a corresponding contact is made easier. The surface of annular electrode 208 in contact with the liquids is preferably coated by an insulating layer. During manufacture of lens 204, the contact surface of the annular foot 209 can be exposed by placing the annular electrode 208 on a flat surface before the insulating coating is applied. The bottom surface of the annular foot 209 is thus shielded, and will not be coated by the insulating layer.

In this example, liquid lens 204 comprises a fixed lens 210 forming one of the windows containing the liquids in the lens.

An inner housing 211 is provided supporting a number of further separate fixed lenses 212. The liquid lens 204 and fixed lenses 212 together form a lens unit having an optical power of a range determined by the variable liquid interface of the liquid lens 204, and a magnitude determined by fixed lenses 210 and 212.

A first contact connects the support 203 to electrode 206, and comprises a conducting track 213a, comprising, for example, a metal such as copper, extending from support 203 within the wall of the lens housing 202 to a sliding contact illustrated schematically by block 214, and a conductive track 213b, for example also formed of copper, extending from the sliding contact 214 to the electrode 206. The sliding contact 214 comprises a first conductive surface 215a connected to conducting track 213a, and a second conductive surface 215b connected to conducting track 213b, the first and second conductive surfaces arranged to make a sliding contact with each other. A second contact connects support 203 to electrode 209, and comprises a conducting track 216a, a sliding contact, illustrated schematically by block 217, and a conducting track 216b. Conducting track 216a for example comprises a metal such as copper, and extends from support 203 within the wall of the lens housing 202 but in a different region from track 213a, to the sliding contact. Conducting track 216b extends from the sliding contact 217 to electrode 209, and in particular, makes contact with annular foot 210. Sliding contact 217 comprises conductive surfaces 218a and 218b connected to conductive tracks 216a and 216b respectively, and which make sliding contact with each other. The first and second contacts thus provide a connection between the liquid lens 204 and circuitry on the support 203 for driving the liquid lens.

While in FIG. 2 the electrodes 206 and 209 are shown as separated from the conductive surfaces 215b and 218b, and connected thereto by conducting tracks 213b and 216b, in alternative embodiments the conductive surfaces 215b and 218b could be in direct contact with the electrodes 206, 209, or the electrodes 206, 209 could themselves form the conductive surfaces 215b and 218b.

An image sensor 219 is mounted on the support 203, and the outer lens housing 202 is mounted over the image sensor 219 such that images received via the liquid lens 204 are formed on the image sensor 219 and can be captured. Driving circuitry 220 is preferably mounted on support 203 for providing drive signals for driving the liquid lens 204.

During assembly, the liquid lens 204 and the inner housing 211 are fixed together, for example with glue. The separation between the liquid lens 204 and each of the fixed lenses is carefully controlled.

During calibration, the lens unit comprising liquid lens 204 and fixed lenses 212 in inner housing 211 is moved closer to or further from the image sensor 218, as indicated by the up and down arrows in FIG. 2. As shown schematically by blocks 214 and 217 in FIG. 2, the connections between the support 203 and the electrodes 206 and 209 of the liquid lens are arranged to allow the connection to be established at any final position of the lens unit. In particular, the sliding contacts 214 and 217 each comprise two sliding conducting surfaces that allow movement of these surfaces with respect to each other in the same direction as the allowed movement between the inner and outer housings 211, 202. This allows a connection to be established at any of the possible final positions of the liquid lens along the optical axis Δ. Furthermore, according to certain embodiments, this allows connections to be maintained during positioning of the liquid lens along the optical axis of the lens system. Examples of particular embodiments of the general concept illustrated in FIG. 2 will now be described with reference to FIGS. 3 to 7.

Figure 3A:
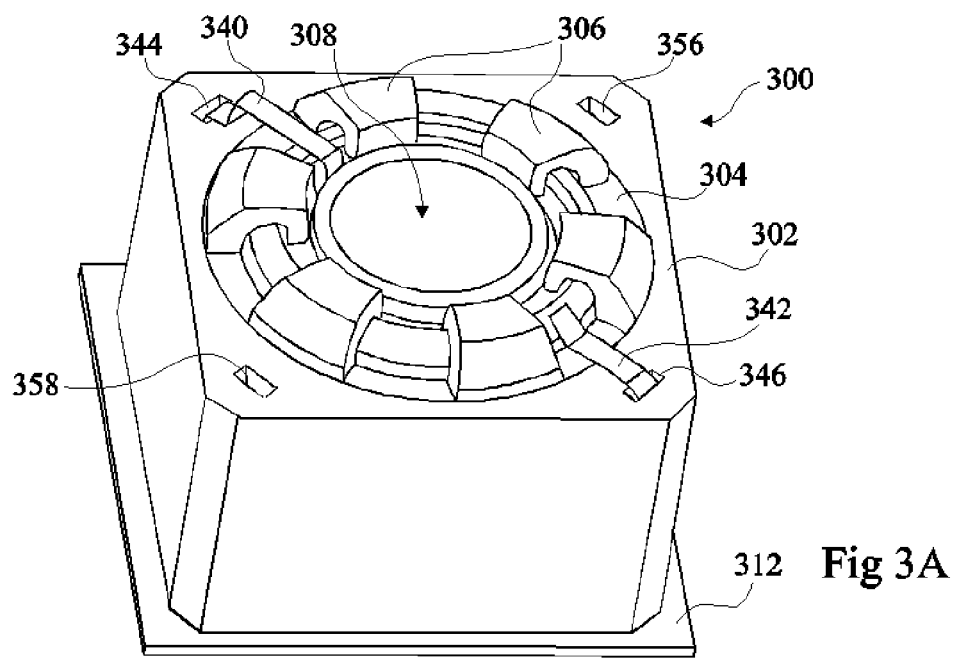
FIG. 3A is an elevation view of a camera module according to an embodiment of the present invention.
Figure 3B:
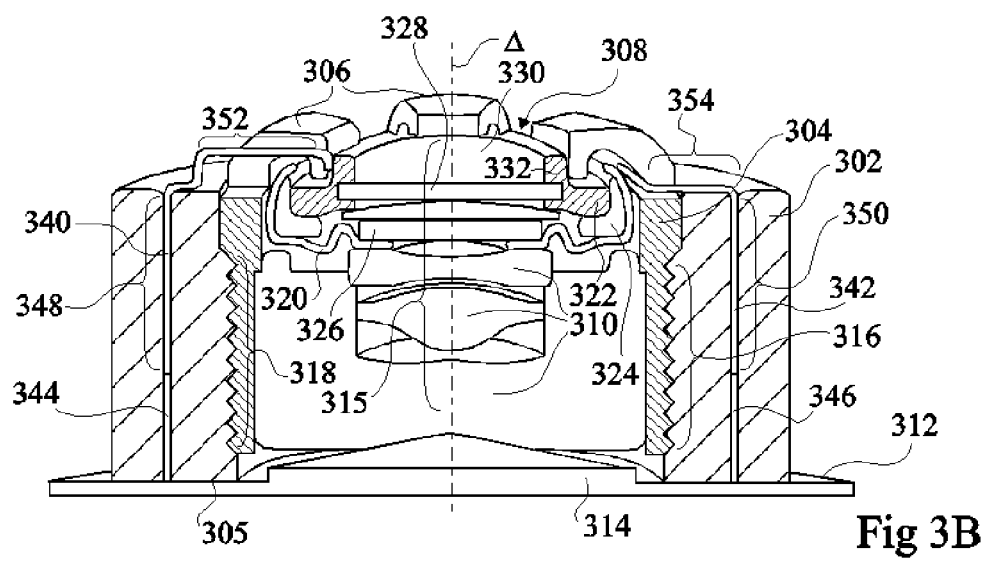
FIG. 3B is a cross-section view of the camera module of FIG. 3A.

FIGS. 3A and 3B illustrate a camera module 300 comprising an outer housing 302 and an inner housing 304, each for example moulded in plastic. The outer housing 302 comprises an underside 305 for mounting to a circuit board and is formed having a substantially cubical outer shape, and a circular hole passing through it, centered on the optical axis Δ of the lenses of the camera module. The inner housing 304 is substantially cylindrical in shape and centered on optical axis Δ, and is positioned within the circular hole in the outer housing 302. The inner housing 304 forms a lens barrel that houses a number of lenses. At the top side it comprises a number of arms 306, in this example six arms, that are evenly spaced in a circle around the top surface of the inner housing 304, and hold the lenses in position. In particular, the inner housing 304 houses a liquid lens 308 and a number of fixed lenses 310. The outer housing 302 is mounted to a circuit board 312, and in particular is aligned over a rectangular image sensor 314, which is mounted on the circuit board 312. Circuit board 312 for example comprises driving circuitry (not shown in FIGS. 3A and 3B) that generates the drive signals for driving liquid lens 308.

The liquid lens 308 and fixed lenses 310 together form a lens unit 315 of lenses having optical powers, shapes and positioning with respect to each other to provide desired optical characteristics. The positioning of the lens unit is calibrated with respect to the image sensor 314 by moving the inner housing 304 with respect to the outer housing 302. In particular, in this example the inner housing 304 has a cylindrical outer surface having an external threaded region 316. The outer housing 302 has a corresponding cylindrical inner surface corresponding to the wall of the hole through the outer housing 302, with an internal threaded region 318. External and internal threaded regions 316 and 318 contact each other such that by rotating the inner housing 304 within the outer housing 302, the inner housing is moved closer to or further from the image sensor 314. The use of threaded adjustment means is advantageous as it allows the positioning of the lens unit to be finely adjusted along the optical axis Δ in a controlled manner by a rotation of the lens unit, while keeping the lens unit centered on the optical axis Δ.

As shown in FIG. 3B, liquid lens 308 is similar in structure to lens 10 described above, and comprises an annular cap 320 and annular body 322 separated by a gasket 324. The liquid chamber is formed between a planar window 326 mounted across the opening through the annular cap 320 and a planar window 328 mounted across the opening through the annular body 322. A planar-convex lens 330 is also mounted in this example across the opening through annular body 322 with its planar side against the planar lens 328. The cap 320 forms one electrode of the lens, and contacts the conducting liquid in the lens. The annular body 322 forms the second electrode insulated from the liquid-liquid interface, and comprises an annular foot 332 which provides both a support surface for mounting lens 330 and a contact surface easier for making contact with annular body 322.

In this embodiment the lens is mounted with the cap 320 downwards, closest to the image sensor, and the annular body 322 and annular foot 332 facing upwards, away from the image sensor. This orientation has the advantage of making the annular foot 332 more accessible.

Two metal sliding contacts 340, 342 are provided for contacting the electrodes 320, 322 of the liquid lens. Each contact 340, 342 extends partway into a respective hole 344, 346 formed in the outer housing 302. Holes 344, 346 extends from the top surface of the outer housing 302 to the underside 305, and are lined with thin conducting layers (not shown in the figures). The thin conducting layers are for example formed using MID (multiple interconnected devices) technology such as a plastic galvanizing technique. Such a technique involves filling the holes with a chemical solution comprising metal particles such that the holes are plated with metal. The plastic of the walls around the holes 344, 346 is for example particle charged, encouraging coating by metal particles from the chemical solution.

Each contact 340, 342 is substantially L-shaped, and comprises a vertical portion 348, 350, respectively, which extends into the corresponding hole 344, 346, and a substantially horizontal portion 352, 354, respectively, which extends from the top of the vertical portion towards the center of the liquid lens. Horizontal portion 352 of contact 340 extends to the annular foot 322, and curves downwards at its end to make contact with the outer surface of the annular foot facing away from optical axis Δ. Horizontal portion 354 of contact 342 extends to the cap 320, and curves upwards slightly at its end to make contact with the outer surface of cap 320 facing away from the optical axis Δ.

The vertical portions 348, 350 of the contacts 340, 342 comprise one or more conductive surfaces in contact with one or more conductive surfaces within respective holes 344, 346. These conductive surfaces are slidable with respect to each other, in directions substantially parallel to the optical axis Δ of the lens system, allowing contact to be made at various positions of the contacts 340, 342 in each hole.

Assembly of the camera module 300 involves mounting the outer housing 304 on the circuit board 312 aligned with the image sensor 314, for example using glue, placing the lenses 310 and liquid lens 308 in the inner housing 302, and then screwing the inner housing 304 into the outer housing 304. The positioning of the inner housing 302, and thus the lens unit 315 is calibrated, for example by activating the image sensor, rotating the inner housing 304, and detecting when a focused image is achieved. Once this is complete, contacts 340 and 342 are pushed into position into holes 344, 346, to a level such that they make contact with electrodes 320 and 322. Within each hole, at least one conductive surface of each contact makes a sliding contact with at least one conductive surface in each hole. Because these electrodes are able to slide up and down within holes 344, 346, while always contacting the conductive lining of the holes, their height can be regulated to the calibrated height of the liquid lens.

As shown in FIG. 3A, the horizontal portion 352, 354 of contacts 340, 342 are aligned so that they pass through the space between adjacent arms 306. This is advantageous as if the contacts 340, 342 extended over the arms 306, this would increase the height of the camera module, whereas by passing through spaces between arms, the height of the camera module need not be increased. In this example, holes 344, 346 are formed in opposite corners of the substantially square-shaped top surface of the outer housing 302. In the example of FIG. 3A, after calibration of the lens unit 315, the inner housing 302 has been rotated to a position such that holes 344 and 346 are aligned with the spaces between adjacent arms 306, and thus the contacts 340, 342 can be placed in holes 344, 346 and can pass through the spaces between arms 306.

However, it may be that after calibration, holes 344, 346 are aligned with arms 306 rather than the spaces between the arms. The outer housing 302 further comprises two further holes 356, 358 formed in the other two opposite corners of the top surface of the outer housing 302. Holes 356, 358 are identical to holes 344 and 346 in that they extend down to the underside 305 of the outer housing, and are lined with a thin conducting layer. Holes 356, 358 are arranged to be aligned with spaces between arms 306 when holes 344, 346 are aligned with arms 306. The position of the four holes 344, 346, 356, 358 and the positioning of the arms 306 are thus chosen, as will be explained in more detail below with reference to FIG. 4, such that one pair of opposite holes is always aligned with the spaces between arms, and can thus be place in position. If the use of holes 344, 346 is not possible, the contacts can be placed in holes 356, 358 instead.

The thin conducting layers in the holes 344, 346, 356 and 358 are connected by conducting tracks in circuit board 312 to drive circuitry (not shown) that generates the required drive voltages for the liquid lens. The thin conducting layers of holes 344 and 356 are for example both connected to an output of the drive circuitry for providing a voltage to annular foot 332, while the thin conducting layers of holes 346 and 358 are for example both connected to an output of the drive circuitry for providing a voltage to the cap 320. Thus when contact 340 is placed in hole 344, or hole 356, and contact 342 is placed in hole 346, or hole 358, the liquid lens is connected correctly.

Figure 4:
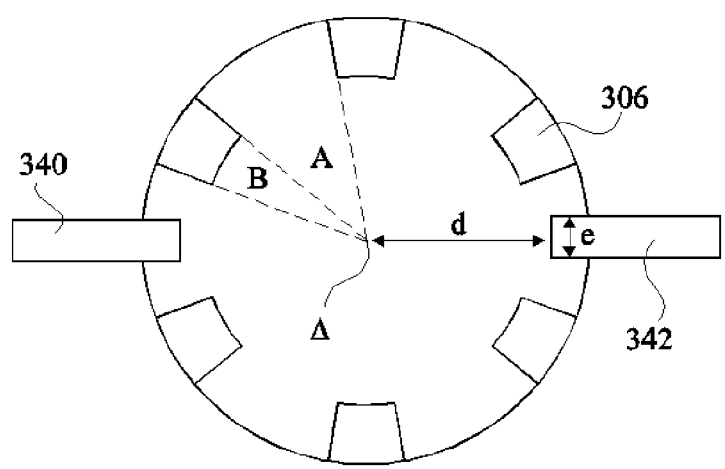
FIG. 4 is a diagram schematically illustrating spacing of contacts of FIGS. 3A and 3B.

FIG. 4 will be used to for illustrating a general rule for the arrangement of the arms 306 such that there is no dead angle, in other words such that the two contacts can always be positioned between adjacent arms. In FIG. 4, "e" represents the widths of contacts 340 and 342, which are the same size in this example, "d" represents the distance from the contact to the centre of the inner housing 304 (also the optical axis), "A" is the angular size of the space between arms in radians (assuming that the space is the same between each arm), and "B" is the angular size of the arms in radians (assuming the arms are equal in size). To avoid a dead angle, A, B, e and d should e chosen such that:

$$A > B + 2 \cdot e/d$$

This formula applies whatever the number of arms that are provided.

Figure 5:
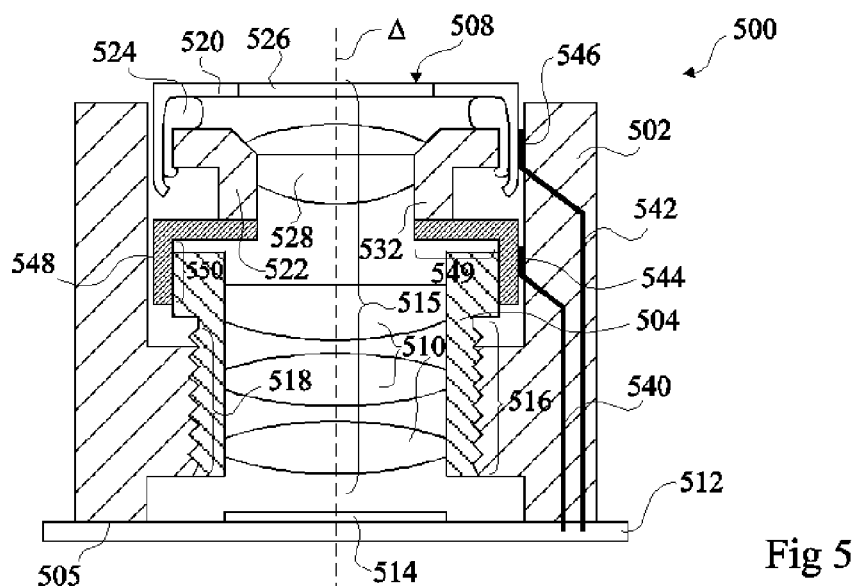
FIGS. 5 to 7 are cross-section views of camera modules according to embodiments of the present invention.
Figure 6:
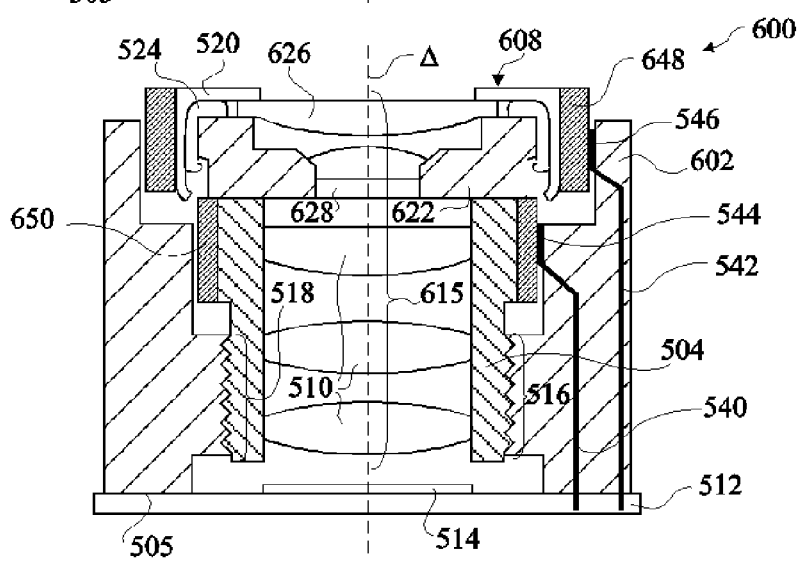
Figure 7:
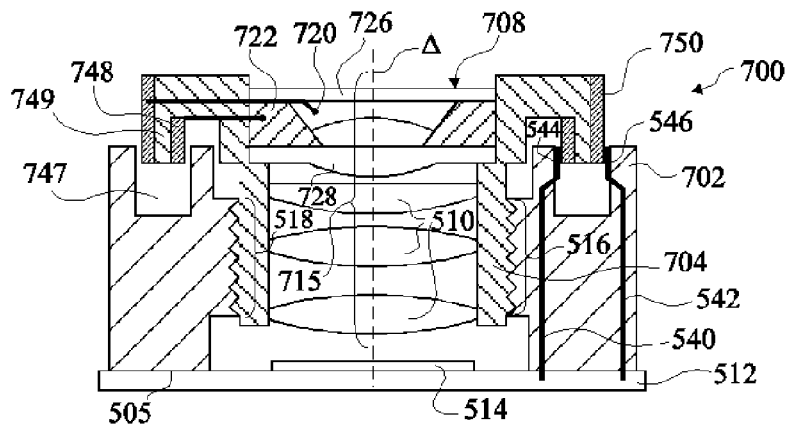

FIGS. 5 to 7 illustrate camera modules in which contact is maintained between the drive circuitry (not shown in the figures) and the electrodes of the liquid lens throughout calibration. This allows the possibility of controlling the liquid lens during calibration, which is advantageous in some embodiments. In particular, in cases where the liquid interface of the liquid lens provides no optical power only when a given voltage is applied, it may be preferable to apply the given voltage during calibration. Furthermore, in some embodiments the voltage needed for the liquid lens to have no power may not be known, and thus a range of voltages may need to be applied during calibration.

With reference to FIG. 5, a camera module 500 comprises an outer housing 502 and an inner housing 504, both of which are substantially cylindrical in shape and centered on an optical axis of lenses in the camera module. The inner housing 504 is positioned within the outer housing 502. The outer housing 502 comprises an underside 505 for mounting to a circuit board. A liquid lens 508 is provided in a top region of the outer housing 502, and the inner housing is provided below the liquid lens 508. The inner housing forms a lens barrel that houses a number of fixed lenses 510. The outer housing 502 is mounted at its underside 505 to a circuit board 512, aligned over a rectangular image sensor 514 provided mounted on the circuit board 512. Circuit board 512 comprises driving circuitry that generates the drive signals for driving liquid lens 508.

The liquid lens 508 and fixed lenses 510 together form a lens unit 515. The positioning of the lens unit 515 is calibrated with respect to the image sensor 514 by moving the inner housing 504 with respect to the outer housing 502. In particular, in this example the inner housing 504 has a cylindrical outer surface having a threaded portion 516. The outer housing 502 has a corresponding cylindrical inner surface with a corresponding threaded region 518. Threaded portions 516 and 518 contact such that by rotating the inner housing 504 within the outer housing 502, the inner housing is moved closer to or further from the image sensor 514.

Liquid lens 508 is similar in structure to liquid lens 308 above, and comprises an annular cap 520 and annular body 522 forming electrodes of the liquid lens, separated by a gasket 524. However, in liquid lens 508 the liquid chamber is formed between a planar window 526 mounted across the opening through the annular cap 520 and a planar-convex lens 528 mounted across the opening through the annular body 522. The annular body 522 comprises an annular foot 532 extending in this case downwards, making electrical contact with the annular body easier.

In this embodiment the liquid lens 508 is mounted with the cap 520 at the top, and the annular body 522 closest to the image sensor 514.

Two metal contacts 540, 542 are provided for contacting the electrodes 520, 522 of the liquid lens 508. Each contact 540, 542 extends within the wall of the outer housing 502 from the underside 505 of the outer housing, where it makes contact with tracks of the circuit board 512 connected to the drive circuitry, to a point on the inner surface of the wall of the outer housing. Contact 540 exits the wall of the outer housing 502 at a point in the inner surface where a contact member 544 is provided. Contact 542 exits the wall of the outer housing 502 at a point higher up in the inner surface of the outer housing, where a contact member 546 is provided.

The annular foot 532 of liquid lens 508 is mounted on a metal ring 548, for example using a conductive glue. Metal ring 548 is for example L-shaped in cross-section, comprising a horizontal section 549 on which annular foot 532 is mounted, and a vertical section 550 extending downwards from the outer edge of the horizontal section.

Contact members 544 and 546 each comprise conductive surfaces that make contact with the annular outer conductive surface of the vertical section 550 of metal ring 548 and with the annular outer conductive surface of cap electrode 520 respectively. The vertical dimensions of vertical section 550 of ring 548 and the outer wall of cap 520 are relatively large and thus contact can be made between these surfaces and the contact members 544, 546 over a range of vertical positions of the inner housing 502. Thus as the inner housing 502, upon rotation, moves upwards or downwards with respect to the outer housing 504, contact is maintained with the contacts 540, 542.

FIG. 6 illustrates an embodiment of a camera module 600, which is similar to camera module 500 of FIG. 5, and like parts have been labelled with like reference numerals and will not be described again in detail.

In the embodiment of FIG. 5, the contact members 544, 546 are vertically separated from each other, but are both provided at the same distance from the optical axis Δ. In the embodiment of FIG. 6, the contact members 544, 546 in the outer housing 602 are at different distances from the optical axis Δ, as well as being separated vertically. In particular, contact member 546 for the liquid lens 608 is in a region of the hole through the outer housing 602 having a greater diameter that the region comprising contact member 544. This arrangement avoids accidental contact or shorting of the contact members when the inner housing 504 is screwed into the outer housing 602.

A metal ring 648 is provided outside of the liquid lens 608 to act as an interface between the edge of the cap 520 and the contact member 546. In particular, ring 648 has an outer conductive surface that contacts with a conductive surface of contact member 546.

Liquid lens 608 is different from liquid lens 508 in that it comprises a fixed lens 626 traversing the hole in the cap 520, and a planar lens traversing the hole in the annular body 622. Furthermore, annular body 622 does not comprise the annular foot in this embodiment, but instead a further metal ring 650 is provided, the top of which contacts the underside of annular body 622, and the outer side of which provides a conductive surface that contacts a corresponding conductive surface of the contact member 544. Both the outer conductive surface of metal ring 648 and the outer side of metal ring 650 make slidable contact with contact members 544, 546 respectively, thereby allowing vertical movement of the inner housing 504 while maintaining the contact between these surfaces.

FIG. 7 illustrates a further alternative arrangement in which the contact members 544, 546 in the outer housing are now provided at the same vertical height as each other, but separated from each other by being at different distances from the optical axis Δ. Contact members 544, 546 are provided at opposite sides of an annular trench 747 running around the top surface of the outer housing 702. Trench 747 is for example square in cross-section. The inner housing 704 comprises an annular protrusion 749 extending downwards from the top portion of the inner housing, also substantially square in cross-section, which enters the trench 747. Annular protrusion 749 comprises a metal ring 748 on a radially inner surface and a metal ring 750 on a radially outer surface, these rings being for example formed by metal plating formed on the walls of the annular protrusion 749. As the annular protrusion 749 descends into trench 747, metal rings 748, 750, contact with the contact members 544, 546 respectively. In particular, each metal ring comprises at least one conductive surface that makes a slidable contact with the contact members 544, 546 respectively. Thus as the inner housing 704 is rotated with respect the outer housing 702, the inner housing 704 ascends or descends, and thus annular protrusion 749 ascends or descends in trench 747, while contact is maintained between the metal rings 748, 750 and the contact members 544, 546.

In the embodiment of FIG. 7, the liquid lens 708 is mounted directly in the inner housing 704. Liquid lens 708 has a three layer structure, comprising a planar lens 726 and a planar convex lens 728 sandwiching an annular electrode 722. A second electrode 720 is provided that makes contact with the conducting liquid in the lens. The metal rings 748 and 750 are connected to the electrodes 720, 720, for example by wires.

The embodiments of FIGS. 5, 6 and 7 are all susceptible to variations. For example, the body portions of the liquid lenses 508, 608, 708, forming electrodes 522, 622 and 722 in the figures could be combined with the inner housing 504, 704 of each embodiment to form a single element. Such a single element therefore comprises a surface, which is conical in the examples, for supporting and centering the edge of the liquid interface of the liquid lens, one or more further surface for receiving fixed lenses 510, and a surface 516 providing the interface with the outer housing 502, 602, 702, in the example provided by a threaded region. Such a single element has the advantage of making it easier to provide a determined spacing between the inner housing and the variable lens, and also makes it easier to align the liquid interface of the liquid lenses with the fixed lenses and the outer housing. Alternatively, the body portions of the liquid lenses forming electrodes 522, 622 and 722 could comprise a surface for receiving some or all of the fixed lenses 510, and be mechanically connected, for example using glue, to the inner housing 504, 704, which for example houses no fixed lenses or some of the fixed lenses 510, and which comprises the surface 516 for contacting the outer housing 502, 602, 702.

Thus housings for a liquid lens have been described that allow the position of the liquid lens be calibrated and contact between the electrodes of the lens to be made either after calibration, as is the case with the embodiment of FIGS. 3A and 3B, or during and after calibration, as is the case with the embodiments of FIGS. 5 to 7. In the latter case, the voltage to be applied during calibration to achieve a calibration optical power of the liquid lens, for example in which the liquid lens has no optical power, may not be know prior to calibration, and can be determined during calibration, at the same time as positioning of the lens system with respect to the image sensor. The embodiments described comprise inner and outer housings that respectively form portions moveable with respect to each other to allow calibration of the positioning of the lenses with an image sensor.

The housing described herein can be incorporated in a range of devices, in particular electronics devices such as compact digital cameras, mobile telephones, endoscopes, etc. While in the example embodiments in the figures the positioning of the lens unit is controlled by providing threaded regions on respective contacting cylindrical surfaces, radially outwards of the lens unit from the optical axis Δ and centered on the optical Δ, in alternative embodiments the position could be adjusted using different means. For example, it will be apparent to those skilled in the art that one or more threaded bolts could be provided that engage with the inner and outer housing such that turning the bolts moves one housing with respect to the other. Alternatively, the inner and outer housings could be slidable with respect to each other, and when in the final position they can be fixed in position by glue, or other fixing means such as a bolt or a screw for example screwed into both the inner and outer housing, for example transversally. Furthermore, while the outer region is described as comprising an internal thread and the inner region an external thread, given a different arrangement the types of threads could be inversed.

Having thus described at least one illustrative embodiment of the invention, various alterations, modifications and improvements will readily occur to those skilled in the art. Such alterations, modifications and improvements are intended to be within the spirit and scope of the invention. Accordingly, the foregoing description is by way of example only and is not intended to be limiting. The invention is limited only as defined in the following claims and the equivalent thereto. Zone Name: A1,AMD Zone Name: A2,AMD,M

The invention claimed is:

1. A housing for a variable focus liquid lens containing first and second immiscible liquids defining a liquid-liquid interface moveable by electrowetting by application of a voltage between first and second electrodes of the liquid lens, the housing comprising:
a first portion comprising a contact surface for contact with a circuit board;
a second portion for receiving the liquid lens, the second portion arranged to be moveable with respect to said first portion in a first direction parallel to an optical axis (Δ) of the liquid lens when said liquid lens is positioned in said housing; and
first and second contacts for electrically coupling the circuit board to the first and second electrodes respectively of the liquid lens when said liquid lens is positioned in said housing, wherein each of the first and second contacts comprises a first conductive surface arranged to make contact with a second conductive surface, wherein said first and second conductive surfaces are slidable with respect to each other in said first direction, so that the circuit board is coupled to the first and second electrodes.

2. The housing of claim 1, wherein the first portion comprises a first threaded region and the second portion comprises a second corresponding threaded region, the second portion being moveable with respect to the first portion in said first direction by rotating said second portion with respect to the first portion.

3. The housing of claim 1, wherein said second portion comprises a region for receiving at least one fixed lens.

4. The housing of claim 1, wherein the first conductive surfaces of the first and second contacts are formed of conductive layers lining first and second holes passing through said first portion, and said second conductive surfaces of the first and second contacts comprise first and second metal contacts positioned within said first and second holes, respectively.

5. The housing of claim 4, wherein said second portion comprises a plurality of arms spaced radially around an end of said second portion for holding said liquid lens in position, wherein said first and second metal contacts extend between adjacent ones of said arms to make contact with said first and second electrodes respectively of the liquid lens, when said liquid lens is positioned in said housing.

6. The housing of claim 5, further comprising a further pair of holes, lined with a conducting layer, for receiving said metal contacts for coupling said electrodes of the liquid lens to the circuit board, wherein the further pair of holes are positioned such that when said first and second holes are aligned with one or more of said arms, said further pair of holes are aligned with spaces between said arms.

7. The housing of claim 1, wherein the first conducting surfaces of the first and second contacts comprise first and second contact members positioned on a surface of said first portion, and wherein said second conducting surface of at least one of said first and second contacts comprises one of said first and second electrodes of said liquid lens, said electrode being annular.

8. The housing of claim 7, wherein said first and second contact members are separated from each other radially.

9. The housing of claim 7, wherein said first and second contact members are separated from each other in said first direction.

10. The housing of claim 1, wherein the first conducting surfaces of the first and second contacts comprise first and second contact members positioned on a surface of said first portion, and said second conducting surfaces of at least one of said first and second contacts comprises a metal ring arranged as an interface between said contact member and said first and second electrodes.

11. A lens system comprising:
a variable focus liquid lens containing first and second immiscible liquids defining a liquid-liquid interface moveable by electrowetting by application of a voltage between first and second electrodes of the liquid lens;
a housing for said variable focus liquid lens, the housing comprising:
a first portion comprising a contact surface for contact with a circuit board,
a second portion on which the liquid lens is mounted, the second portion arranged to be moveable with respect to said first portion in a first direction parallel to an optical axis (Δ) of the liquid lens when said liquid lens is positioned in said housing, and
first and second contacts for electrically coupling the circuit board to the first and second electrodes respectively of the liquid lens, wherein each of the first and second contacts comprises a first conductive surface arranged to make contact with a second conductive surface, said first and second conductive surfaces being slidable with respect to each other in said first direction, so that the circuit board can be coupled to the first and second electrodes; and
at least one fixed lens mounted to said second portion.

12. The lens system of claim 11, wherein said variable focus liquid lens comprises at least one fixed lens.

13. The lens system of claim 11, wherein said variable focus liquid lens comprises an annular electrode comprising an annular foot, said annular foot comprising:
a surface having rotational symmetry about an optical axis of said variable focus liquid lens and arranged to make contact with said first contact, and
a cap arranged to make contact with said second contact.

14. A camera module comprising the lens system of claim 11, mounted on a circuit board, and drive circuitry mounted on said circuit board, wherein the drive circuitry is connected to said first and second contacts and arranged to generate drive signals for driving said variable focus liquid lens.

15. The camera module of claim 14, further comprising an image sensor mounted to said circuit board, said lens system being mounted over said image sensor in order to provide an image to said image sensor.

16. A method of calibrating the focusing of the camera module of claim 15, comprising:
adjusting the distance between said lens system and said image sensor and at the same time applying a given voltage to at least one of said first and second contacts to set the liquid-liquid interface of the liquid lens in a nominal position, wherein adjusting comprises moving said second portion with respect to said first portion.

17. An electronics device comprising the camera module of claim 14.

18. A method of manufacturing a camera module of claim 14, wherein the camera module comprises a housing for a variable focus liquid lens containing first and second immiscible liquids defining a liquid-liquid interface moveable by electrowetting by application of a voltage between first and second electrodes of the liquid lens, the housing comprising:
- a first portion comprising a contact surface for contact with a circuit board;
- a second portion for receiving the liquid lens, the second portion arranged to be moveable with respect to said first portion in a first direction parallel to an optical axis (Δ) of the liquid lens when said liquid lens is positioned in said housing; and
- first and second contacts for electrically coupling the circuit board to the first and second electrodes respectively of the liquid lens when said liquid lens is positioned in said housing, wherein each of the first and second contacts comprises a first conductive surface arranged to make contact with a second conductive surface, wherein said first and second conductive surfaces are slidable with respect to each other in said first direction, so that the circuit board is coupled to the first and second electrodes, wherein the first conductive surfaces of the first and second contacts are formed of conductive layers lining first and second holes passing through said first portion, and said second conductive surfaces of the first and second contacts comprise first and second metal contacts positioned within said first and second holes, respectively, and wherein said second portion comprises a plurality of arms spaced radially around an end of said second portion for holding said liquid lens in position, wherein said first and second metal contacts extend between adjacent ones of said arms to make contact with said first and second electrodes respectively of the liquid lens, when said liquid lens is positioned in said housing, wherein the method comprises:

focusing said lens system by moving said second portion to a final position with respect to said first portion;

determining that in the final position said first and second holes are not aligned with said arms; and placing said metal contacts in said first and second holes to a position in which they contact said first and second electrodes.

\* \* \* \* \*